United States Patent [19]

Vaschillo et al.

[11] Patent Number: 5,997,482
[45] Date of Patent: Dec. 7, 1999

[54] THERAPEUTIC METHOD FOR A HUMAN SUBJECT

[76] Inventors: Evgeny G. Vaschillo, 9952 SW. 8 St., #219, Miami, Fla. 33174; Naphtali David Rishe, 100 Lincoln Rd. #1547, Miami Beach, Fla. 33139

[21] Appl. No.: 09/088,155

[22] Filed: Jun. 1, 1998

[51] Int. Cl.$^6$ ...................................................... A61N 5/00
[52] U.S. Cl. .......................... 600/484; 600/529; 600/500; 129/897
[58] Field of Search ..................................... 600/300–301, 600/479–508, 529–538, 544; 129/897–899; 434/265

[56] References Cited

U.S. PATENT DOCUMENTS 4,832,038   5/1989   Arai .

OTHER PUBLICATIONS

"Voluntary Control of the Slow–Wave Heart Rhythm Structure: Cardio–Vascular System Frequency Analysis", E.G. Vaschillo et al; Academy of Physical Culture (Russia) 29 pages.

"Voluntary Control of the Slow–Wave Heart Rhythm Structure;Humans Ability To Volumtarily Control Heart Rhythm", Evegeny Vaschillo et al; Academy of Physical Culture (Russia), 20 pages.

"Respiratory Sinus Arrhthmia Versus Neck/Trapezius EMG and Incentive Inspirometry Biofeedback for Asthma: A Pilot Study", Paul Lehrer et al. Applied Psychophysiology and Biofeedback, Vo. 22, Nov. 97, 15 pages.

*Primary Examiner*—Cary O'Connor
*Assistant Examiner*—Michael Astorino
*Attorney, Agent, or Firm*—Herbert Dubno

[57] ABSTRACT

A therapeutic method includes determining heartbeat and respiratory rates converted in respective electric signals of a subject, displaying the heart rate, spectrally analyzing the respiratory and heartbeat signals, thereby defining a phase shift therebetween, causing the subject to modify the respiratory rate in a sense tending to minimize the phase shift and selecting a frequency of the displayed reference signal which correlates with the modified respiratory signal, and establishing an optimum reference signal displayed as a resonance frequency unique for the subject upon approaching the zero phase shift between the heart signal and the modified respiratory signal.

7 Claims, 6 Drawing Sheets

F I G. 2

FIG. 3A (TESTING SINUS)

FIG. 3 B
(HEART RATE)

FIG.4A

TRANSFER FUNCTIONS

*BREATHING HEART-RATE*

FIG.4B

TRANSFER FUNCTIONS

BREATHING - HEART RATE

THERAPEUTIC METHOD FOR A HUMAN SUBJECT

FIELD OF THE INVENTION

The present invention relates to a method of self-management and relaxation leading to restoring balance in the central and vegetative nervous systems, to normalizing vegetative function and to the treatment of a variety of disorders including asthma and heart arrhythmia. More particularly this invention concerns a therapeutic method for a human subject which determines an optimal relationship between respiratory frequency and heartbeat unique for any given patient by utilizing Fourier analysis.

BACKGROUND OF THE INVENTION

It is known to utilize methodologies teaching relaxation which are directed at improving a patient's health. Many of these methods are based on correcting respiratory habits.

It has been suggested that the human cardio-vascular system can be regulated by using biofeedback methods. It has been further found that a human organism does indeed possess the possibility of feed back control or regulation of arterial blood pressure by changing the tone of blood vessels. It has been also found that the cardiovascular system generates by exhibiting high amplitude slow-wave oscillations which are superimposed upon the heartbeat. In practical terms such high amplitude low-frequency oscillations were associated with a tendency to decrease psycho-emotional strain, reduced tiredness and reduced chronic agitation (Vashillo E. G. et al, Research of Resonance Characteristics of a Cardio-vascular system, USSR Academy, 257 (1983)).

Based upon this discovery a therapeutic method was presented which comprised the steps of:

(a) registering a continuous heartbeat signal corresponding to a current heartbeat frequency of a patient;

(b) converting the heartbeat signal to a an electrical signal to display the latter on a screen;

(c) simultaneously with (b) displaying a reference signal corresponding to the low-frequency signal with high amplitude signal empirically determined prior to the experiment; and (d) modifying the patient behavior to gradually adjust the amplitude of the electric signal.

During the treatment a patient observed a signal corresponding to his present heartbeat rhythm and adjusted the latter to a plurality of sequentially shown sinusoidal signals with 13,12,11,10,9 and 7 second periods respectively. A frequency of that sinusoidal electric signal which provided a maximum amplitude of the signal corresponding to the patient's current heart rate oscillations has been defined as the "resonance" signal (Chernigovskaya N .B. et al, Voluntary Regulation of Cardio Vascular System for Correction of Functional Conditions of a Patient Suffering from Nerousis, USSR Academy of Science, 58 (1990)).

Thus method was both time consuming (taking approximately one hour) and imprecise because the determination of the "resonance" frequency was based on six discrete attempts corresponding to respective periods of the above mentioned sinusoidal signals. Although the "resonance" frequency only slightly depends on a given condition of a patient, an hour long procedure still can undesirably affect precision of determination of such frequency.

It has been also reasoned that "[T]he immediate cardio-vascular effects of respiration summate with the baroreceptor reflexes to produce a "resonance frequency"... expected to increase the amplitude of heart oscillations." P. Lehrer, E. Vashillo., et al., Respiratory Sinus Arrhythmia Versus Neck/Trapezius EMG an Incentive Inspirometry Biofeedbak for Asthma: A pilot Study, Applied Psychophysiology and Biofeedback, vol. 22, 97 (1997). The results were consistent with Vashillo's theory that RSA (respiratory sinus arrhythmia) biofeedback "exercises homeostatic autonomic reflex mechanism through increasing the amplitude of cardiac oscillation." Id., at 95.

However a concrete relationship between the respiratory and heartbeat frequencies has been developed heretofore in this context.

The U.S. Pat. No. 4,580,575 describes a method of correcting the failure of heartbeat by employing heartbeat and respiration detection circuits. However the latter is done for controlling upper and lower heartbeat limits beyond which a patient's life may be in jeopardy.

OBJECTS OF THE INVENTION

A principal object of the invention is to provide an efficient and reliable biofeedback method for self-management and relaxation.

Another object of the present invention is to provide a method for individually determining an optimal relationship between respiratory and heartbeat frequencies utilizing Fourier analysis.

Still another object is to provide an assembly or apparatus for implementing the method according to the invention.

SUMMARY OF THE INVENTION

The present invention is based on a Respiratory Sinus Arrhythmia (RSA) physiological mechanism which we have found to be critical to the coordination of respiration and cardiovascular system functions.

The inventive method uses respiration and through RSA powerfully impacts the cardiovascular system. The high amplitude oscillation of cardiovascular functions generated by breathing produce training, stimulating and normalizing impacts onto reflex mechanics regulating these function. The whole procedure's impact on the user is therapeutic.

The assembly according to the invention for determining an optimal breathing frequency:

first means for registering a subjects's current respiration rate and for converting the latter into a first electrical signal;

second means for registering a current heartbeat of the subject and for converting the latter into a second electrical signal;

monitor means operatively connected with the second means for displaying the second signal and a reference signal juxtaposed with the second signal and having a frequency arbitrarily selected from a predetermined frequency range;

processing means for spectrally analyzing the first and second electrical signals and for generating a resulting signal corresponding to a phase shift therebetween;

selecting means operatively connected with the processing and display means for selecting another frequency from the predetermined range of the displayed reference signal in response to the resulting signal, the other frequency being so selected as to gradually minimize the phase shift.

We have found that a person can impose a high-amplitude low-frequency oscillations upon his or her cardiac rhythm in the frequency range of 0.01–0.14 Hz. Further, within this range, every individual has a unique "resonance" frequency which, when these oscillations reach their highest amplitude, the patient recognizes a general well being and improvement in a variety of therapeutic conditions.

Our experiments have shown further that the cardiovascular system of a healthy adult has well defined resonance frequencies in the range of 0.055–0.14 Hz. The resonance frequency lying within this range is specific for every individual and varies insignificantly in response to her psycho-emotional condition. These high amplitude oscillations of cardiovascular functions can be controlled by breathing produce training using the reflex mechanics regulating these functions.

The inventive system is selfadjustable. The goal of such adjustment is to determine such patient's respiratory frequency which is accompanied by high amplitude or resonance oscillations of the patient's cardiovascular system.

Further the main criterion of control of the resonance frequency according to the invention is synchronization of heart and breath oscillations or, in other words, a zero or minimum phase shift therebetween.

The method of selfadjustment at the resonance frequency can thus comprise:

a) continuously measuring heartbeat and respiratory rates of a subject and converting the rates into respective heart sinusoidal and respiratory electrical signals;

b) selecting a sinusoidal reference signal with a first frequency lying in a frequency range of 0.01 to 0.14 Hz;

c) simultaneously displaying the reference and heart signals to the patient d) instructing the patient to modify the respiratory rate according to the sinusoidal reference signal;

e) spectrally analyzing the respiratory and heartbeat signals, thereby defining a phase shift therebetween;

f) controllably selecting another frequency of the displayed reference signal within the predetermined range thereby minimizing the phase shift obtained in step (e);

g) repeating steps (c) through (f) until the phase shift between the heart signal and the modified respiratory signal approaches "0" thereby determining an optimum breathing frequency corresponding to a resonance frequency wave characteristic unique for the patient's cardiovascular system; and i) training the patient to impose high-amplitude oscillations at the resonance frequency upon his heart rate.

The maximum amplitude of the resonance heartbeat signal corresponds to the optimal breathing frequency which the patients can either see on a screen or be informed of by any other display means.

The step of determining a phase shift between the respiratory and heart waves can include the steps of:

$f_1$) decreasing the respiratory rate if the phase shift is less than zero, and $f_2$) increasing the respiratory rate if the phase shift is more than zero.

As a result of the described inventive method and after training based thereupon, a subject can easily impose high-amplitude oscillations on her heart rate at the respective resonance frequency unique to her. The statistical data showing some rather limited examples of a positive impact of the method according to the invention is as follows:.

pulse rate decreases to an average 7–10 beats per minutes among children and to 5–6 beats per minute among athletes arterial pressure is normalized;

the blood circulation in peripheral parts of the body improves; and the speed of voluntary muscle relaxation increases.

All of the above effects increase when a person is trained in accordance with the inventive method. The reasons causing the relaxation effect are the following:

imposing slow wave oscillation on blood pressure in all arterial blood vessels, even the smallest ones;

stimulation of the brain by baroreceptor impulses; and training of the central and autonomic nervous systems.

Figure 4A:
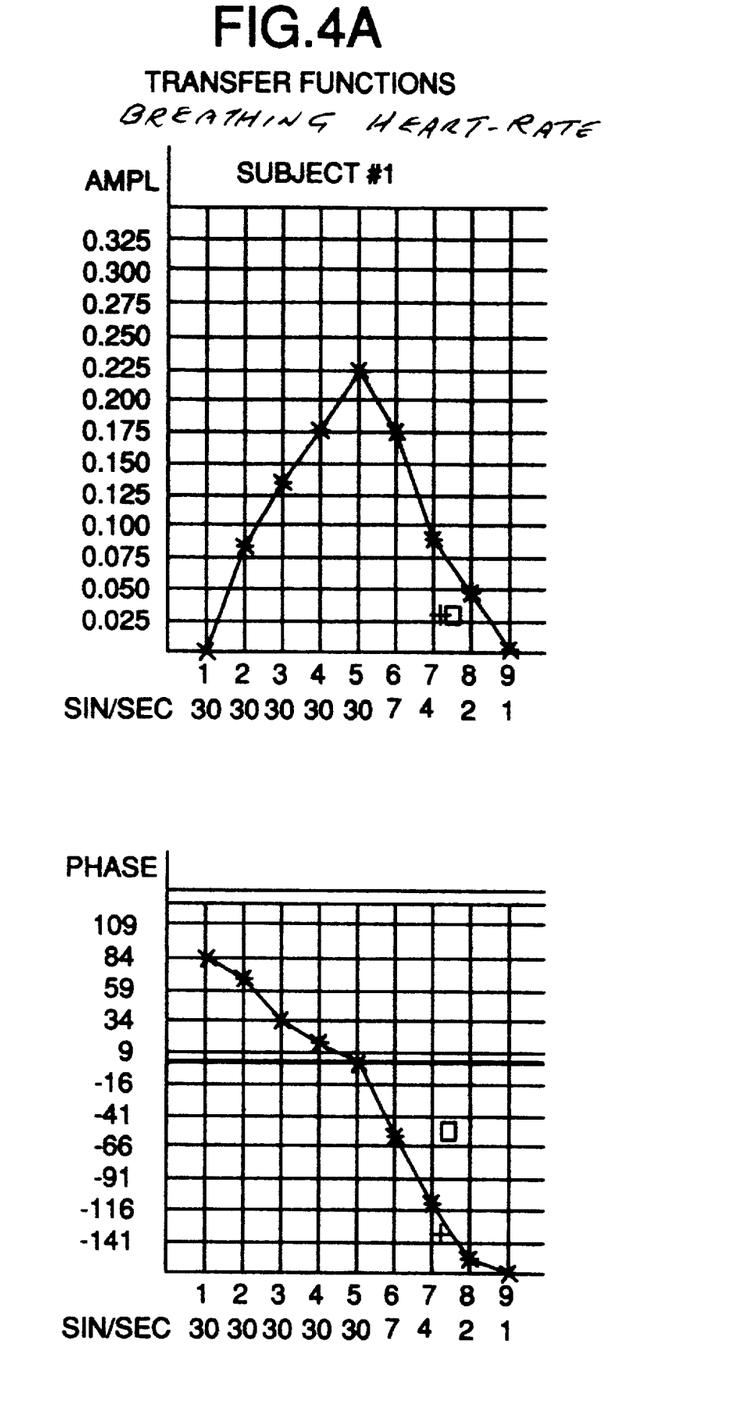
FIG. 4 is respective transfer functions between heart rhythm and respiration magnitude for two patients.
Figure 4B:
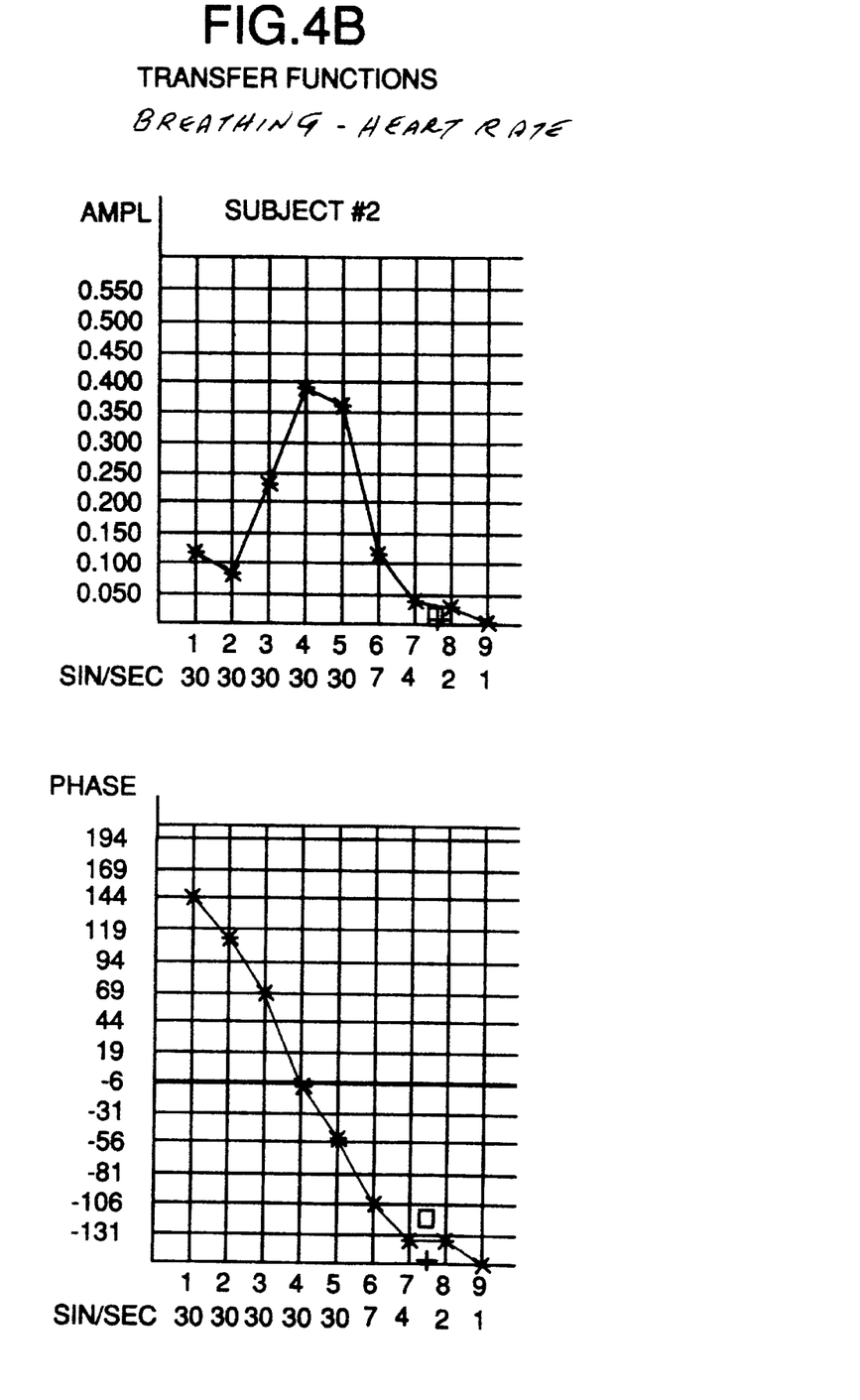

All studied subjects developed a self-acquired ability to control their own HR (heart rate) and were able to reproduce the harmonic oscillations within a frequency range 0.01–0.14 Hz with distinctive amplitude (reaching high ± 25 beats per minutes in the middle of the range) corresponding to a testing sinus with a period of 100, 47, 34, 18, 13, 9 and 7 seconds. Having focused on the investigation of RSA and the links between heart rhythm and respiration magnitude we obtained phase transfer functions therebetween which were calculated for the 0.03–0.5 Hz frequency range. The phase function has positive values at low frequencies as can be seen in FIG. 4 described herebelow. Upon increasing the respiratory frequency, phase function values lower to negative values. At the frequency of the magnitude function's maximum the values of the phase function approach zero. The ideal respiratory frequency corresponding to the maximum of the magnitude function and the maximum amplitude is unique for each subject.

The clearly defined maximum of the amplitude function shows the resonance characteristic of the human cardiovascular system. Respiration in the resonance frequency swings high amplitude oscillations of the heart rate. Amplitude at the resonance frequency is determined by a closed-loop resonance characteristic rather than by respiration intensity or the level of the heart rate.

The example of the curative properties of the inventive method has shown the following:

30 subjects of professionally trained athletes whose ages ranged from 19 to 22 years old were selected. Using further random selection half of the subjects has been assigned to the control group and the other half to the experimental group. The experimental group underwent 20 minutes of relaxation respiration procedure once a day for 10 consecutive days. All subjects were tested using a special polymyographical procedure on the first, fifth and tenth days. The procedure has been designed to reveal existing voluntary muscle relaxation disorders, to evaluate inhibition activity and to process balance in the central nervous system.

Balance has been measured as a ratio of top speed voluntary muscle, quadriceps femoris. Inhibitory activity has been estimated based on the period and structure of voluntary muscle relaxation.

As a result, muscular relaxation disorders disappeared in the experimental group after 10 days of therapy, and rates of relaxation increased. A significant difference has been found between the mean start values and final values (p>0.001). The nervous process balance has been restored. The main changes became after the fourth relaxation respiration procedure. Without the described relaxation procedure such normalization of the central nervous system would be possible through many months of relaxation training and meditation. The training procedure can be successfully applied to treating bronchial asthma, neuroses, heart rate disorders, disorders of autonomic nervous system and to decrease psychological tension.

In the practice of the invention the method can employ the steps of:

(a) displaying a position of an image on a display to the subject while controlling the position by the heartbeat of the subject;

(b) causing the subject, by control of a breathing pattern of the subject, to voluntarily shift the image in a targeted manner on the display, thereby superimposing upon the heartbeat the resonance frequency wave characteristic of the subject; and (c) conditioning the subject to produce the resonance wave by controlling the respiratory rate of the subject for improvement of a biological or emotional state of the subject.

In another aspect of the invention the training method can comprise:

(a) measuring heartbeat of the patient;

(b) subjecting the heartbeat of the patient measured in step (a) to a Fourier analysis to determine a resonance frequency superimposed on the heartbeat and specific to the patient in a frequency range of 0.01 to 0.14 Hz;

(c) monitoring of the resonance frequency while instructing the patient to breathe at faster and slower rates until a breathing rate of the patient matches the resonance frequency and a phase difference between the breathing rate and the resonance frequency is at a minimum; and (d) conditioning the patient to breathe at that rate which matches the resonance frequency and the phase difference is at the minimum.

Advantageously this method further comprises the steps of:

(e) displaying a sine wave representing the resonance frequency on a display screen viewable by the patient;

(f) displaying a wave representing an actual breathing rate of the patient on the same screen; and (g) demonstrating to the patient progressive approach of waves to a condition of minimum phase difference.

BRIEF DESCRIPTION OF THE DRAWING

The above and other features, objects and advantages will become more readily apparent from the following description illustrated by the following drawing in which.

SPECIFIC DESCRIPTION

Figure 1:
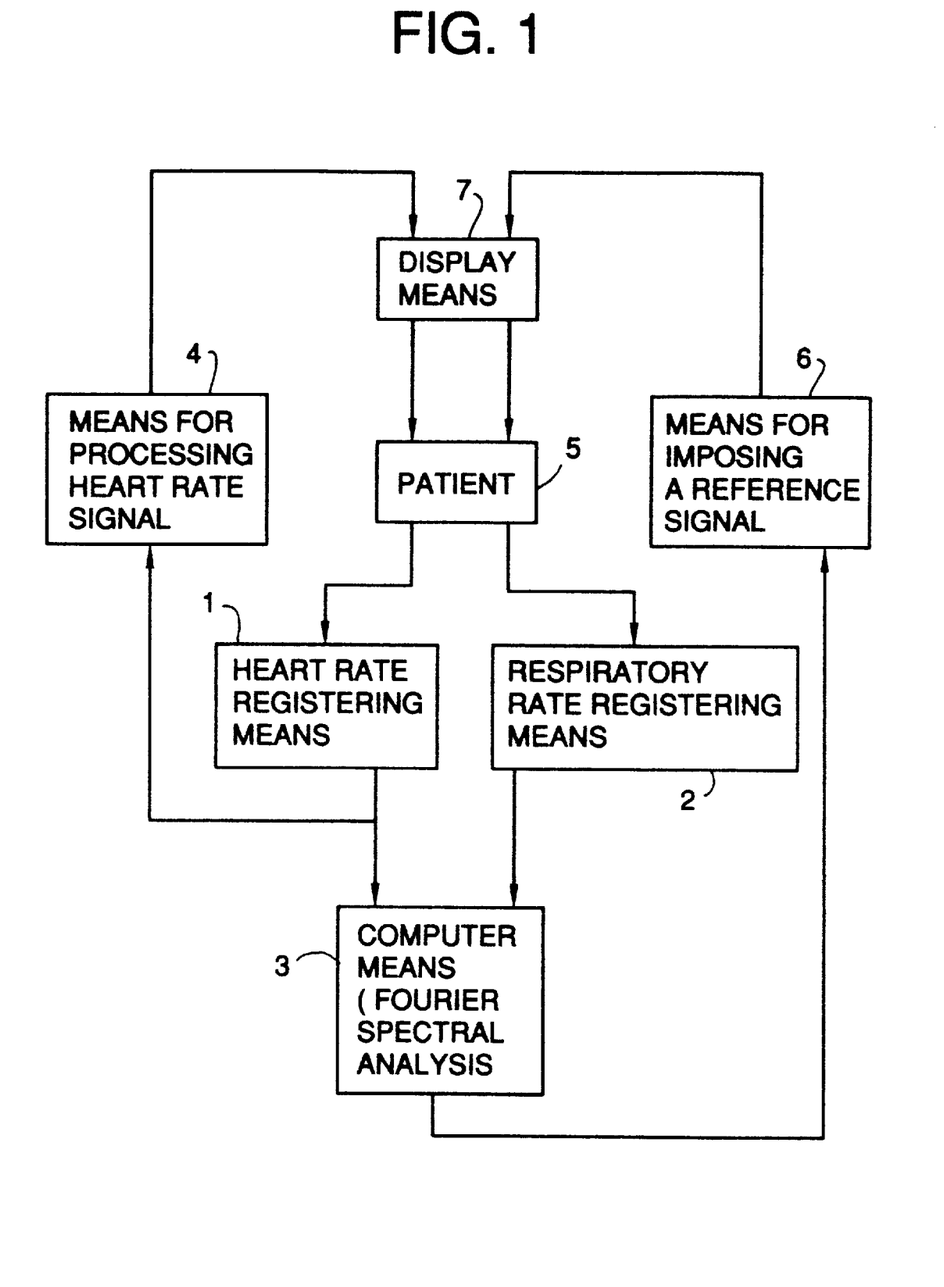
FIG. 1 is a block diagram of the method according to the invention.

As is seen in a block diagram illustrated in FIG. 1 a subject's 5 heart rate and respiratory rate are registered by respective register means 1 and 2. The rates are further converted into respective heart and electrical signals received and processed by a computer means 3 utilizing Fourier spectral analysis to determine a phase shift between the signals.

Upon registering the current heart beat, the latter is processed by means 4 for further demonstration thereof to the subject by display means 7.

The computer means 3 determining the phase shift is connected with a means 6 for determining an optimal reference signal with a resonance frequency corresponding to the zero phase shift.

Fourier Filtration (FF) was performed by the following (Eykhoff) algorithm:

$$C(w_i) = (2 \div U_o T) \int_o^T Y(t) \operatorname{Sin}(w_i t) dt$$

$$D(w_i) = (2 \div U_o T) \int_o^T Y(t) \operatorname{Cos}(w_i t) dt$$

$T = KT_1$ $T_1 = 2\P/w_i$ where:

T—the time of the task (30–60 seconds);

K—integer;

$U_o$—amplitude of the testing sinusoidal signal; and

Y(t)—the process (heart rhythm and respiratory curve); and $W_i$—the frequency of a modified reference signal.

Thus the values of real $C(w_i)$ and imaginary $D(w_i)$ parts of the frequency characteristic were received. Using these parts we calculated the amplitude $A(w_i)$ and phase $\phi(w_i)$ frequency characteristics of the observed process:

$$A(w_i) = \{C(W_i)^2 + D(W_i)^2\}^{1/2}$$

$$\phi(W_i) = \operatorname{arctg}\{D(W_i) \div C(W_i)\}.$$

Considering that the amplitude of the testing sinusoidal signal corresponded to the variation of HR (heart rate) for ± 30 beats per minute, the amplitude of the reproduced HR harmonic of $i^{th}$ harmonic in the spectrum of the observed process $\operatorname{Ampl}(w_i)$ was calculated using the formula:

$\operatorname{Ampl}(w_i) = \pm 30 A(w_i)$ beats per minute.

Once the optimal signal with the resonance frequency corresponding to the zero phase shift is determined the display means 7 convey to the subject two signals one of which is the subject's heartbeat and the other the optimal signal at the respective resonance frequency known to be unique for the subject.

Figure 2:
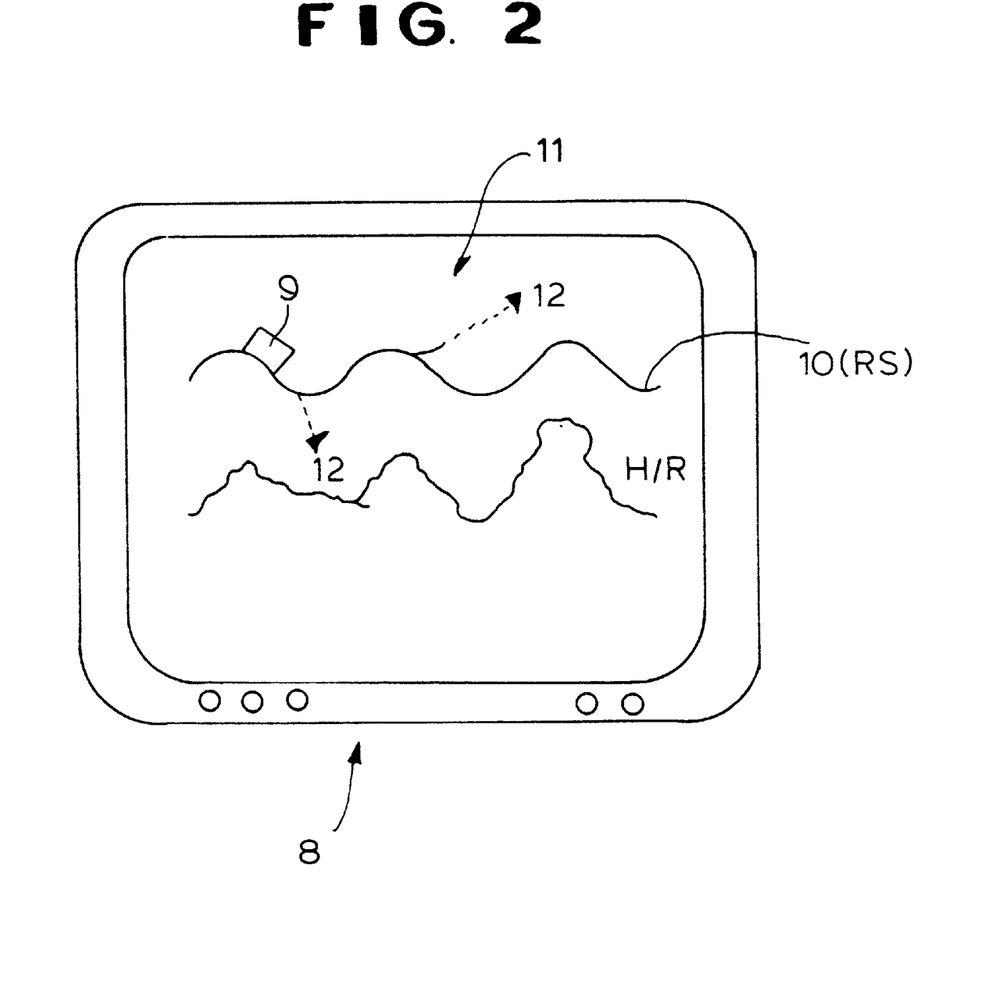
FIG. 2 is a schematically shown assembly according to the invention.

FIG. 2 shows diagrammatically a practical implementation of the above described principle method shown in FIG.1. While display means 7 can be any means for instructing the subject to follow the chosen reference signal, the most convenient means has been found to be the visual one demonstrating two sinusoids of the heart rate signal and the modified reference signal one under the other.

The subject is positioned in front of a visual display 8 showing any graphic object 9 displaceable along the course 10 corresponding to the reference signal having the resonance frequency which has been determined according to the inventive method explained above. Since the user knows and is trained to breath at her unique resonance frequency the object driven by the heart rate signal corresponding to the resonance frequency is on its predetermined course 10 which, the case illustrated in FIG. 2 is the sinusoid representing the reference signal. Yet if the user deviates from his or her trained breathing rate corresponding to the resonance frequency of the reference signal it is immediately demonstrated by a screen means 11 on which the object 9 visually diverges from the course 10 along arrows 12. The subject is able, upon modifying her breathing in response to the instruction given on the screen means 11, to steer the object back to the predetermined curse 10. For example, if the reference sinusoid (RS) is leading thus making the phase shift be below zero and therefore steering the object off the course 10, then the patient is asked to lower his or her respiratory frequency to bring the object back to the course 10 and conversely, if the phase shift is above zero the subject is instructed to increase his breathing rate.

As a result of the training the subject is able to impose the slow high-magnitude oscillation onto his heart rhythm with the frequency of his cardio vascular system's resonance. Thus, the average heart rate decreases and the peripheral blood circulation improves.

The screen means can also be with a numerical score registering the subject's success in achieving the goals.

Figure 3A:
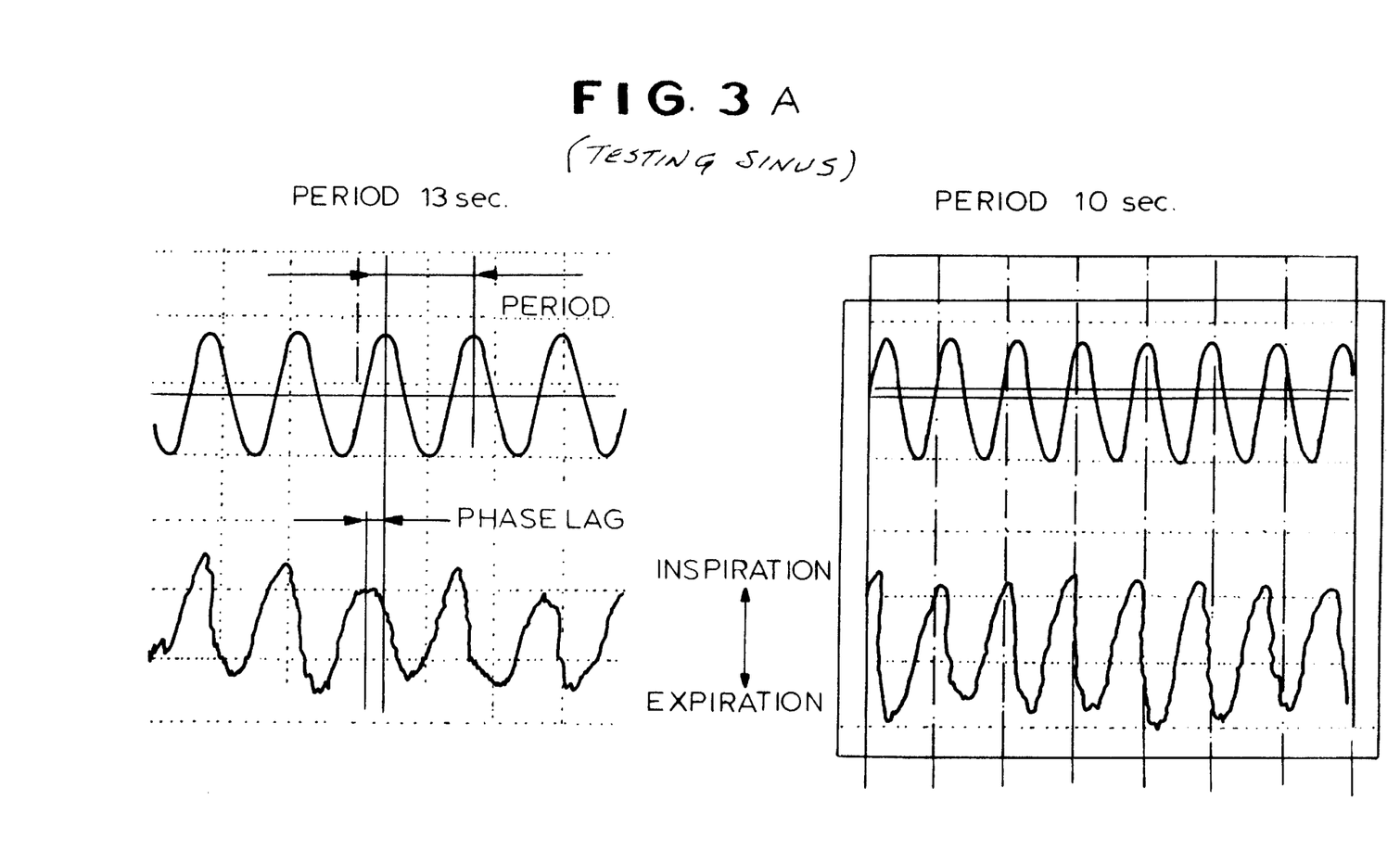
FIG. 3 is the respective graphs showing the results of the experiments conducted according to the inventive method.
Figure 3B:
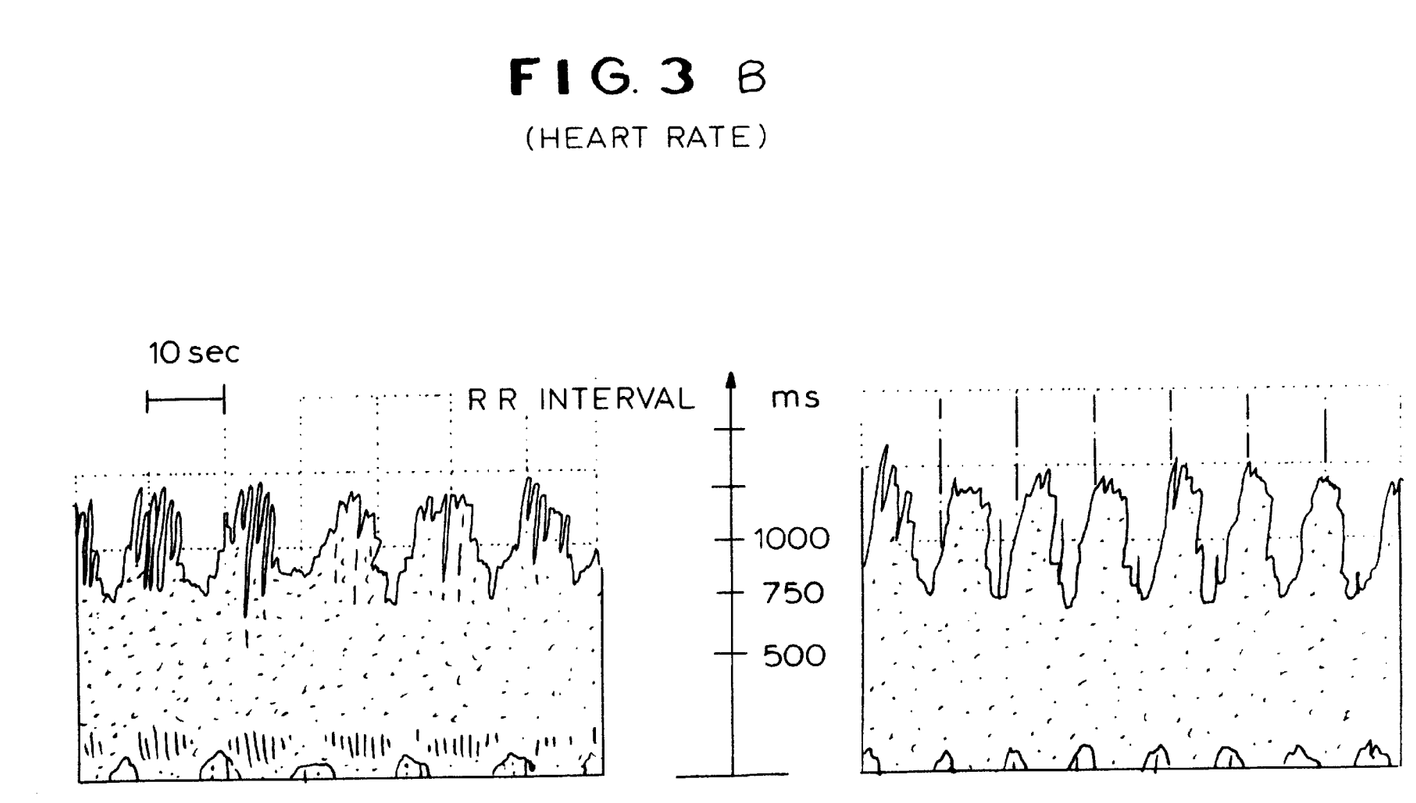

FIG. 3 illustrates the testing sinus signals with 13 second period. The phase lag is clearly seen on the user's breathing graph and offers the user a visual guide for modifying the breathing pattern to bring the lag to a minimum.

As is mentioned above FIG. 4 demonstrates phase transfer functions between heart rhythm and respiration magnitude calculated for the 0.03–0.5 Hz frequency range. Clearly positive values of the phase function are obtained at low frequencies whereas, upon increasing the respiratory frequency, phase function values lower to negative values. The values of the phase function are around zero at the frequency of the magnitude function's maximum. The ideal respiratory frequency is unique for each of two subjects as seen on two graphs of FIG. 4.

We claim:

1. A therapeutic method comprising the steps of:
   (a) continuously measuring heartbeat and respiratory rates of a subject and converting the rates into respective heart sinusoidal and respiratory electrical signals;
   b) selecting a sinusoidal reference signal with a first frequency lying in a frequency range of 0.01 to 0.14 Hz;
   c) simultaneously displaying the reference and heart signals to the patient
   d) instructing the patient to modify the respiratory rate according to the sinusoidal reference signal;
   e) spectrally analyzing the respiratory and heartbeat signals, thereby defining a phase shift therebetween;
   f) controllably selecting another frequency of the displayed reference signal within said predetermined range thereby minimizing the phase shift obtained in step (e);
   g) repeating steps (c) through (f) until the phase shift between the heart signal and the modified respiratory signal approaches "0" thereby determining an optimum breathing frequency corresponding to a resonance frequency wave characteristic unique for the patient's cardiovascular system; and
   i) training the patient to impose high-amplitude oscillations at said resonance frequency upon his heart rate.

2. The method defined in claim 1 wherein the step of determining a phase shift between respiratory and heart rates includes the steps of:
   $f_1$) decreasing the respiratory rate if the phase shift is less than zero, and
   $f_2$) increasing the respiratory rate if the phase shift is more than zero.

3. The therapeutic method defined in claim 1 further comprising the steps of:
   (i) displaying a position of an image on a display to said subject while controlling said position by the heartbeat of the subject;
   (ii) causing said subject, by control of a breathing pattern of the subject, to voluntarily shift said image in a targeted manner on said display, thereby superimposing upon said heartbeat the resonance frequency wave characteristic of the subject; and
   (iii) conditioning said subject to produce said resonance wave by controlling the respiratory rate of the subject for improvement of a biological or emotional state of the subject.

4. A method of training a patient to improve a physical state of the patient, comprising the steps of:
   (a) measuring heartbeat of the patient;
   (b) subjecting the heartbeat of the patient measured in step (a) to a Fourier analysis to determine a resonance frequency superimposed on the heartbeat and specific to the patient in a frequency range of 0.01 to 0.14 Hz;
   (c) monitoring of said resonance frequency while instructing the patient to breathe at faster and slower rates until a breathing rate of the patient matches said resonance frequency and a phase difference between the breathing rate and said resonance frequency is at a minimum; and
   (d) conditioning the patient to breathe at that rate which matches said resonance frequency and said phase difference is at said minimum.

5. The method defined in claim 4, further comprising the steps of:
   (e) displaying a sine wave representing said resonance frequency on a display screen viewable by the patient;
   (f) displaying a wave representing an actual breathing rate of the patient on the same screen; and
   (g) demonstrating to the patient progressive approach of waves to a condition of minimum phase difference.

6. The method defined in claim 5, further comprising the step of displaying a moving image on a display screen deviating to one side and another side of a predetermined path automatically with increase and decrease in heart rate of the patient, and instructing the patient to breathe at such a rate as will maintain travel of said image along said path.

7. An assembly for determining an optimal breathing frequency comprising:
   first means for registering a subjects's current respiration rate and for converting the latter into a first electrical signal;
   second means for registering a current heartbeat of the subject and for converting the latter into a second electrical signal;
   monitor means operatively connected with said second means for displaying said second signal and a reference signal juxtaposed with said second signal and having a frequency arbitrarily selected from a predetermined frequency range;
   processing means for spectrally analyzing the first and second electrical signals and for generating a resulting signal corresponding to a phase shift therebetween;
   selecting means operatively connected with said processing and display means for selecting another frequency from the predetermined range of the displayed reference signal in response to said resulting signal, said other frequency being so selected as to gradually minimize said phase shift.

* * * * *